(12) United States Patent
Chen et al.

(10) Patent No.: US 8,137,687 B2
(45) Date of Patent: Mar. 20, 2012

(54) 4-AZA-CAPROLACTONE-BASED POLYMERIC COMPOSITIONS USEFUL FOR THE MANUFACTURE OF BIODEGRADABLE MEDICAL DEVICES AND AS MEDICAL DEVICE COATINGS

(75) Inventors: Mingfei Chen, Santa Rosa, CA (US); Peiwen Cheng, Santa Rosa, CA (US); Kishore Udipi, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1060 days.

(21) Appl. No.: 12/064,108

(22) PCT Filed: Aug. 9, 2006

(86) PCT No.: PCT/US2006/030952
§ 371 (c)(1),
(2), (4) Date: Feb. 19, 2008

(87) PCT Pub. No.: WO2007/024481
PCT Pub. Date: Mar. 1, 2007

(65) Prior Publication Data
US 2008/0233169 A1    Sep. 25, 2008

Related U.S. Application Data

(60) Provisional application No. 60/711,895, filed on Aug. 25, 2005.

(51) Int. Cl.
| | | |
|---|---|---|
| *A61F 2/04* | (2006.01) | |
| *A61F 2/06* | (2006.01) | |
| *C07D 267/10* | (2006.01) | |
| *C08L 67/00* | (2006.01) | |
| *C08G 63/685* | (2006.01) | |
| *A61K 39/395* | (2006.01) | |

(52) U.S. Cl. ... 424/423; 623/1.49; 623/1.46; 424/130.1; 540/544; 528/361; 525/411; 525/419

(58) Field of Classification Search ........................ None
See application file for complete search history.

(56) References Cited

U.S. PATENT DOCUMENTS

| | | |
|---|---|---|
| 5,670,161 A | 9/1997 | Healy et al. |
| 2003/0108588 A1 | 6/2003 | Chen et al. |
| 2003/0219562 A1 | 11/2003 | Rypacek et al. |
| 2004/0180131 A1 | 9/2004 | Cheng |

FOREIGN PATENT DOCUMENTS

| | | |
|---|---|---|
| WO | WO2004/021976 | 3/2004 |
| WO | WO2007/024501 | 3/2007 |

*Primary Examiner* — Robert A Wax
*Assistant Examiner* — Danah Al-Awadi

(57) ABSTRACT

N-substituted 4-aza-caprolactone biodegradable polymers, including derivatives thereof, useful for making implantable medical devices and coatings therefore are provided. The medical devices and coatings of the present invention can also be used for in situ controlled release drug delivery and are useful for treating or preventing medical conditions such as restenosis, aneurisms and vulnerable plaque.

27 Claims, 5 Drawing Sheets

Polyesters

Poly(ortho esters)

Polyanhydrides

Polyphosphazenes

4-AZA-CAPROLACTONE-BASED POLYMERIC COMPOSITIONS USEFUL FOR THE MANUFACTURE OF BIODEGRADABLE MEDICAL DEVICES AND AS MEDICAL DEVICE COATINGS

FIELD OF THE INVENTION

The present invention relates to new polymeric compositions useful for the manufacture of medical devices and coatings for medical devices, wherein the devices and/or coatings include biodegradable polymers based on 4-aza-caprolactone and its N-substituted derivatives.

BACKGROUND OF THE INVENTION

Implantable medical devices have become increasingly more common over the last 50 years and have found applications in nearly every branch of medicine. Examples include joint replacements, vascular grafts, heart valves, ocular lenses, pacemakers, vascular stents, urethral stents, and many others. However, regardless of the application, implantable medical devices must be biocompatible, that is, they must be fabricated from materials that will not elicit an adverse biological response such as, but not limited to, inflammation, thrombogensis or necrosis. Thus, early medical devices were generally fabricated from inert materials such as precious metals and ceramics. More recently, stainless steel and other metal alloys have replaces precious metals and polymers are being substituted for ceramics.

Generally, implantable medical devices are intended to serve long-term therapeutic applications and are not removed once implanted. In some cases it may be desirable to use implantable medical devices for short-term therapies. However, their removal may require highly invasive surgical procedures that place the patient at risk for life threatening complications. Therefore, it would be desirable to have medical devices designed for short-term applications that degrade via normal metabolic pathways and are reabsorbed into the surrounding tissues.

One of the first bioresorbable medical devices develop was the synthetic absorbable suture marketed as Dexon in the 1960s by Davis and Geck, Inc. (Danbury, Conn.). Since that time, diverse biodegradable polymer-based products have found acceptance as implantable medical devices and implantable medical device coatings, thereby alleviating the need for secondary invasive procedure(s) to remove implanted medical device(s).

Biodegradable polymers can be either natural or synthetic. In general, synthetic polymers offer greater advantages than natural materials in that they can be tailored to give a wider range of properties and more predictable lot-to-lot uniformity than can materials from natural sources. Synthetic polymers also represent a more reliable source of raw materials, ones free from concerns of immunogenicity.

In general, polymer selection criteria for use as biomaterials is to match the mechanical properties of the polymer(s) and degradation time to the needs of the specific in vivo application. The factors affecting the mechanical performance of biodegradable polymers are those that are well known to the polymer scientist, and include monomer selection, initiator selection, process conditions and the presence of additives. These factors in turn influence the polymer's hydrophilicity, crystallinity, melt and glass-transition temperatures, molecular weight, molecular-weight distribution, end groups, sequence distribution (random versus blocky) and presence of residual monomer or additives. In addition, the polymer scientist working with biodegradable materials must evaluate each of these variables for its effect on biodegradation. Known biodegradable polymers include, among others, polyglycolide (PGA), polylactide (PLA) and poly(ε-caprolactone) (PCA). However, these polymers are generally hydrophobic and their structures are difficult to modify. Consequently, the polymer's physical characteristics are difficult to modify, or tune, to match specific clinical demands. For example, polymers made from PLA are extremely slow to degrade and thus not suited for all applications. To address this deficiency polymer scientists have developed co-polymers of PLA and PCA. However, biodegradation rates remain significantly limited.

Additionally, recent advances in in situ drug delivery has led to the development of implantable medical devices specifically designed to provide therapeutic compositions to remote anatomical locations. Perhaps one of the most exciting areas of in situ drug delivery is in the field of intervention cardiology. Vascular occlusions leading to ischemic heart disease are frequently treated using percutaneous transluminal coronary angioplasty (PTCA) whereby a dilation catheter is inserted through a femoral artery incision and directed to the site of the vascular occlusion. The catheter is dilated and the expanding catheter tip (the balloon) opens the occluded artery restoring vascular patency. Generally, a vascular stent is deployed at the treatment site to minimize vascular recoil and restenosis. However, in some cases stent deployment leads to damage to the intimal lining of the artery which may result in vascular smooth muscle cell hyperproliferation and restenosis. When restenosis occurs it is necessary to either re-dilate the artery at the treatment site, or, if that is not possible, a surgical coronary artery bypass procedure must be performed.

Recently, it has been determined drug-eluting stents coated with anti-proliferative drugs such as, but not limited to, rapamycin and its analogs and paclitaxel have shown great promises in preventing restenosis. However, there is a need to develop additional and potentially more efficacious drug-eluting stents (DES). One critical factor in DES efficacy is the drug elution rate. Drug elution is generally a factor of the drug's solubility in the polymer coating applied to the stent.

Presently, bio-stable, that is non-resorbable polymers, are used as drug eluting coatings for metal stents. The polymer scientist has many different options when selecting a suitable bio-stable polymer and recently several of the present inventors have made significant advances in tuning polymer coatings useful for drug elution (see co-pending U.S. patent application Ser. No. 11/005,463). However, the number and type of bioresorbable polymers is much more limited. Therefore, in order for new bioresorbable polymeric medical devices to be developed which have the same functional diversity as their biostable polymer counterparts, it is necessary to first develop new and useful bioresorbable polymers that can be tuned to match drug solubility and provide greater control over resorbability rates.

SUMMARY OF THE INVENTION

The present invention provides biodegradable polymers suitable for use as medical devices and coatings for medical devices. The polymers made in accordance with the teachings of the present invention are biodegradable, biocompatible, amphiphilic and derived from N-substituted 4-aza-caprolactone having the general formula directed below as Formula I:

Formula 1

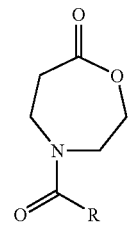

wherein R is a hydrogen, a straight chain or branched $C_1$-$C_{18}$ alkyl, a $C_3$-$C_{18}$ cycloalkyl, a straight chain or branched $C_2$-$C_{18}$ alkenyl or alkynyl, a straight chain or branched $C_1$-$C_{18}$ alkoxy, an aryl, protected carboxyl, a substituted or unsubstituted amino group, an amino acid residue, or hydroxyl. In one particular embodiment R is a methyl group.

The functional pendant group attached to the ring nitrogen provides the resulting polymer (following ring opening polymerization [ROP]) its amphiphilic properties. Moreover, even it left un-substituted, the ring nitrogen also provides the polymer backbone with a secondary amine which is a nucleophile center suitable for post-polymerization polymer modification. Thus the polymers of the present invention are extremely versatile.

In one embodiment of the present invention, N-substituted 4-aza-caprolactone (or its derivative) is copolymerized with D,L-lactide and L-lactide in the presence of an initiator with hydroxyl group(s) such as, but not limited to poly(ethylene glycol) (PEG), 1,6-hexanediol and 1,8-octanediol and then subjected to a ring opening polymerization (ROP) using a suitable catalyst such as, but not limited to, Tin(II) 2-ethylhexanoate to form a polymer having the general structure according to Formula II:

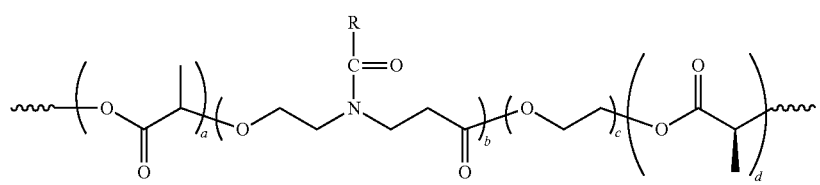

Formula II wherein a:b:c:d are repeating units and wherein a=0-20,000, b=1-20,000, c=1-2000 and d=0-20,000 and R is a hydrogen, a straight chain or branched $C_1$-$C_{18}$ alkyl, a $C_3$-$C_{18}$ cycloalkyl, a straight chain or branched $C_2$-$C_{18}$ alkenyl or alkynyl, a straight chain or branched alkoxy, aryl, protected carboxyl, a substituted or unsubstituted amino group, an amino acid residue, or hydroxyl. In one particular embodiment R is a methyl group.

In another embodiment of the present invention, N-substituted 4-aza-caprolactone or its derivative) is copolymerized with D,L-lactide and L-lactide in the presence of an initiator with hydroxyl group(s) such as, but not limited to poly(ethylene glycol) (PEG), 1,6-hexanediol and 1,8-octanediol and then subjected to ROP using a suitable catalyst such as, but not limited to, Tin(II) 2-ethylhexanoate to form a polymer having the general structure according to Formula III:

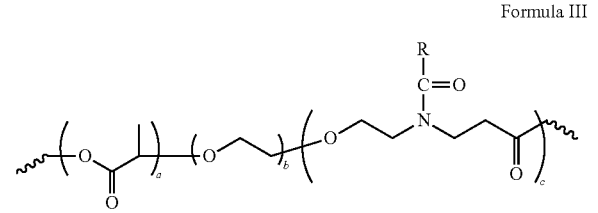

Formula III wherein a:b:c are repeating units for and wherein a=0-20,000, b=1-2000 and c=1-20,000 and R is a hydrogen, a straight chain or branched $C_1$-$C_{18}$ alkyl, a $C_3$-$C_{18}$ cycloalkyl, straight chain or branched $C_2$-$C_{18}$ alkenyl or alkynyl, a straight chain or branched $C_1$-$C_{18}$ alkoxy, an aryl, protected carboxyl, a substituted or unsubstituted amino group, an amino acid residue, or hydroxyl. In one particular embodiment R is a methyl group.

In yet another embodiment of the present invention, N-substituted 4-aza-caprolactone (or its derivative) is copolymerized with D,L-lactide and L-lactide in the presence of an initiator with hydroxyl group(s) such as, but not limited to polyethylene glycol) (PEG), 1,6-hexanediol and 1,8-octanediol and then subjected to ROP using a suitable catalyst such as, but not limited to, Tin(II) 2-ethylhexanoate to form a polymer having the general structure according to Formula IV:

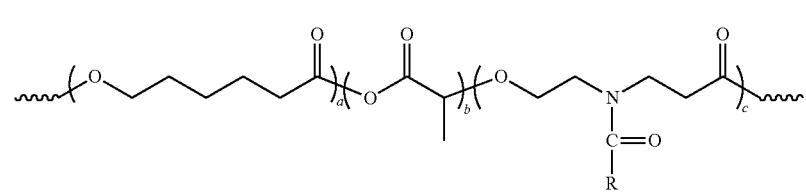

Formula IV wherein a:b:c are repeating units and wherein a=0-20,000, b=1-20,000 and c=1-20,000 and R is a hydrogen, a straight chain or branched $C_1$-$C_{18}$ alkyl, a $C_3$-$C_{18}$ cycloalkyl, a straight chain or branched $C_2$-$C_{18}$ alkenyl or alkynyl, a straight chain or branched $C_1$-$C_{18}$ alkoxy, an aryl, protected carboxyl, a substituted or unsubstituted amino group, an amino acid residue, or hydroxyl. In one particular embodiment R is a methyl group.

In another embodiment of the present invention, N-substituted 4-aza-caprolactone is subjected to ROP using a suitable catalyst such as, but not limited to, Tin(II) 2-ethylhexanoate to form a polymer having the monomer repeating unit for Formula V:

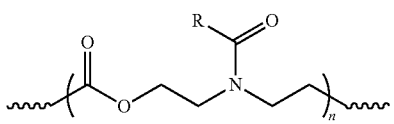

Formula V wherein R is a hydrogen, R is a hydrogen, a straight chain or branched $C_1$-$C_{18}$ alkyl, a $C_3$-$C_{18}$ cycloalkyl, a straight chain or branched $C_2$-$C_{18}$ alkenyl or alkynyl, a straight chain or branched $C_1$-$C_{18}$ alkoxy, an aryl, protected carboxyl, a substituted or unsubstituted amino group, an amino acid residue, or hydroxyl; "n" is any integer from 1 to $10^4$. Moreover, it is also envisioned by the present inventors that N-substituted 4-aza-caprolactone can be co-polymerized with other compounds as disclosed supra such as, but not limited to, lactide, glycolide, δ-caprolactone, dioxanone, trimethyl carbonate, amino acids, peptides, and other to make biodegradable polymers in accordance with the teachings of the present invention.

The present invention also includes implantable medical devices and coatings for medical devices made from one or more of the polymers of the present invention. Moreover, the medical devices and coating made in accordance with the teachings of the present invention include controlled-release coatings wherein one or more bioactive agent is eluted from the polymer in a predetermined fashion. Exemplary embodiments include, but are not limited to, drug-eluting vascular stents and coatings therefore wherein anti-proliferative bioactive agents are released in situ such that restenosis is treated, prevented or inhibited. Suitable bioactive agents include, but are not limited to, FKBP 12 binding compounds such as zotarolimus, estrogens, chaperone inhibitors, protease inhibitors, protein-tyrosine kinase inhibitors, leptomycin B, peroxisome proliferator-activated receptor gamma ligands (PPARγ), hypothemycin, bisphosphonates, epidermal growth factor inhibitors, antibodies, proteasome inhibitors, antibiotics, anti-inflammatories, anti-sense nucleotides and transforming nucleic acids.

Furthermore, the present invention includes the monomers and polymers made in accordance with the teachings of the present invention and include, without limitations a monomer suitable for use in making a polymeric compound comprising the compound of Formula I:

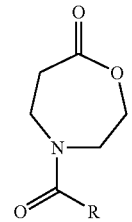

Formula I wherein R is a hydrogen, a straight chain or branched $C_1$-$C_{18}$ alkyl, a $C_3$-$C_{18}$ cycloalkyl, a straight chain or branched $C_2$-$C_{18}$ alkenyl or alkynyl, a straight chain or branched $C_1$-$C_{18}$ alkoxy, an aryl, protected carboxyl, a substituted or unsubstituted amino group, an amino acid residue, or hydroxyl. In one particular embodiment R is a methyl group.

A biodegradable polymer comprising a compound according to Formula II:

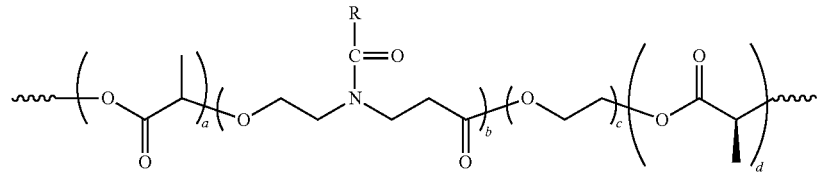

Formula II wherein a:b:c:d are repeating units for each polymer and wherein a=0-20,000, b=1-20,000, c=1-2000 and d=0-20,000 and R is a hydrogen, a straight chain or branched $C_1$-$C_{18}$ alkyl, a $C_3$-$C_{18}$ cycloalkyl, a straight chain or branched $C_2$-$C_{18}$ alkenyl or alkynyl, a straight chain or branched $C_1$-$C_{18}$ alkoxy, an aryl, protected carboxyl, a substituted or unsubstituted amino group, an amino acid residue, or hydroxyl especially wherein R is a methyl group and the repeating units are present in a ratio of 44:11.8:0.2:44; a:b:c:d respectively.

An other embodiment of the present invention includes a biodegradable polymer comprising a compound according to Formula III:

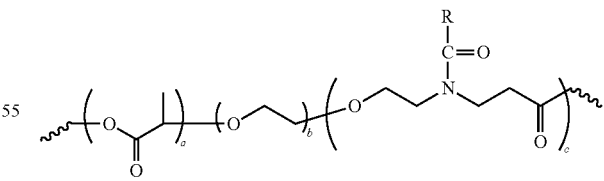

Formula III wherein a:b:c are repeating units for each polymer and wherein a=0-20,000, b=1-2000 and c=1-20,000 and R is a hydrogen, a straight chain or branched $C_1$-$C_{18}$ alkyl, a $C_3$-$C_{18}$ cycloalkyl, a straight chain or branched $C_2$-$C_{18}$ alkenyl or alkynyl, a straight chain or branched $C_1$-$C_{18}$ alkoxy, an aryl, protected carboxyl, a substituted or unsubstituted amino group, an amino acid residue, or hydroxyl In one particular embodiment R is a methyl group and the repeating units are present in a ratio of 99:0.13:0.87; a:b:c respectively.

Also included in the scope of the present invention is a biodegradable polymer comprising a compound according to Formula IV:

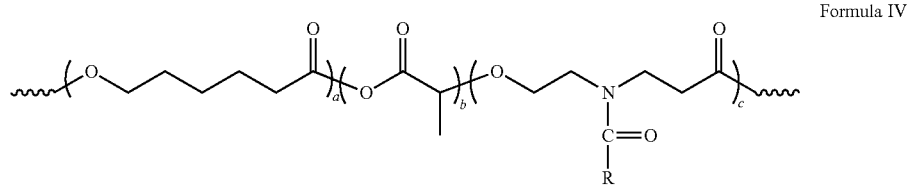

Formula IV wherein a:b:c are repeating units for each polymer and wherein a=0-20,000, b=1-20,000 and c=1-20,000 and R is a hydrogen, a straight chain or branched $C_1$-$C_{18}$ alkyl, a $C_3$-$C_{18}$ cycloalkyl, a straight chain or branched $C_2$-$C_{18}$ alkenyl or alkynyl, a straight chain or branched $C_1$-$C_{18}$ alkoxy, an aryl, protected carboxyl, a substituted or unsubstituted amino group, an amino acid residue, or hydroxyl. In one particular embodiment R is a methyl group and the repeating units are present in a ratio of 3:96:1; a:b:c respectively.

Yet another embodiment of the present invention includes a polymer comprising the monomer according to Formula I and at least one other polymer repeating unit selected from the group consisting of δ-caprolactone, dioxanone, trimethyl carbonate, amino acids, peptides and combinations thereof.

DEFINITION OF TERMS

Figure 1:
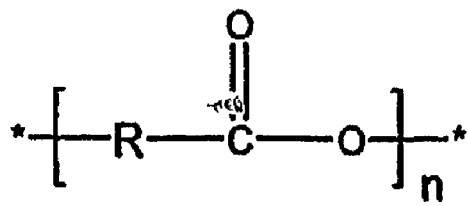
FIG. 1 depicts the chemical structures of the most common biodegradable polymers.
Figure 1:
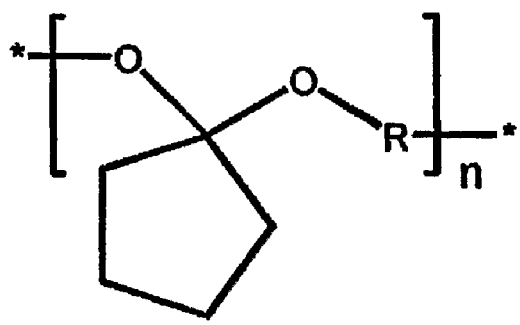
Figure 1:
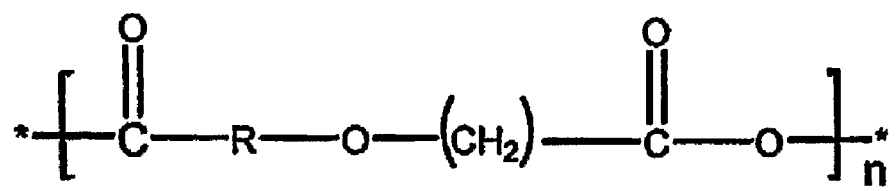
Figure 1:
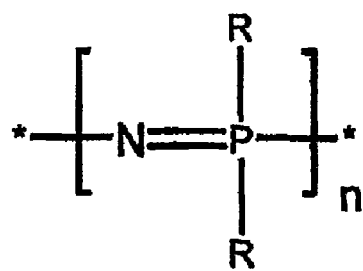

Prior to setting forth the invention, it may be helpful to provide an understanding of the certain terms that will be used hereinafter.

Amphiphilic: As used herein "amphiphilic" shall include compounds having molecules comprising a polar water-soluble group attached to a water-insoluble hydrocarbon chain.

Bioactive agent: As used herein "bioactive agent" shall included anti-proliferative compounds, cytostatic compounds, toxic compounds, anti-inflammatory compounds, analgesics, antibiotics, protease inhibitors, statins, nucleic acids, polypeptides, and delivery vectors including recombinant micro-organisms, liposomes, the like (see Drugs below). The term bioactive agent also encompasses more than one bioactive agent.

Biocompatible: As used herein "biocompatible" shall mean any material that does not cause injury or death to an animal or induce an adverse reaction in an animal when placed in intimate contact with the animal's tissues. Adverse reactions include inflammation, infection, fibrotic tissue formation, cell death, or thrombosis.

Controlled-release: As used herein "controlled-release" refers to the release of a bioactive compound from a medical device surface at a predetermined rate. Controlled-release implies that the bioactive compound does not come off the medical device surface sporadically in an unpredictable fashion and does not "burst" off of the device upon contact with a biological environment (also referred to herein a first-order kinetics) unless specifically intended to do so. However, the term "controlled-release" as used herein does not preclude a "burst phenomenon" associated with deployment. In some embodiments of the present invention an initial burst of drug may be desirable followed by a more gradual release thereafter. The release rate may be steady state (commonly referred to as "timed-release" or zero-order kinetics), that is the drug is released in even amounts over a predetermined time (with or without an initial burst phase) or may be a gradient release. A gradient release implies that the concentration of drug released from the device surface changes over time.

Delayed-Release: As used herein "delayed-release" refers to the release of bioactive agent(s) after a period of time or after an event or series of events.

Drug(s): As used herein "drug" shall include any bioactive agent having a therapeutic effect in an animal. Exemplary, non-limiting examples include anti-proliferatives including, but not limited to, macrolide antibiotics including FKBP 12 binding compounds such as zotarolimus, estrogens, chaperone inhibitors, protease inhibitors, protein-tyrosine kinase inhibitors, peroxisome proliferator-activated receptor gamma ligands (PPARγ), hypothemycin, bisphosphonates, epidermal growth factor inhibitors, antibodies, proteasome inhibitors, antibiotics, anti-inflammatories, anti-sense nucleotides and transforming nucleic acids.

DETAILED DESCRIPTION OF THE INVENTION

Biodegradable polymers, either synthetic or natural, are capable of being cleaved into biocompatible byproducts through chemical- or enzyme-catalyzed hydrolysis. This biodegradable property makes it possible to implant them into the body without the need of subsequent surgical removal. Moreover, drugs formulated with these polymers can be released in a controlled manner, by which the drug concentration in the target site is maintained within the therapeutic window. The release rates of the drugs from the biodegradable polymer can be controlled by a number of factors, such as biodegradation rate, physiochemical properties of the polymers and drugs, thermodynamic compatibility between the polymer and drug and the shape of the medical device.

However, most biocompatible polymers are fairly hydrophobic and are not easily derivatized due to a lack of functional side chains. The most frequently encountered biocompatible polymers are polyesters, polyorthoesters, polyanhydrides and polyphosphazes (see FIG. 1). The present invention provides biodegradable amphiphilic biodegradable polymers used to form the coatings and implantable medical devices of the present invention can generally be described as follows:

To date, conventional biodegradable polymers such as poly (lactide), poly(caprolactone), poly(glycolide) and their copolymers have been used in the manufacture and use of medical devices and medical device coatings, including, but not limited to, those used on and/or in drug delivery devices and suture materials. However, these polymers are generally hydrophobic in nature. The incorporation of hydrophilic materials into these medical device coatings results in these devices and coatings that are more biocompatible and hemocompatible. However, it is understood that the medical device coatings disclosed herein may be comprised of preferably at least about 30%, by weight, more preferably at least about 50%, by weight, and most preferably at least about 80%, by weight, of amphiphilic, biocompatible, biodegradable polymers based on derivatives of N-substituted 4-aza-caprolactone (see Formula I). Of course, the biodegradable polymer of the present invention may be incorporated either individually or in combination with of any conventional polymer in a medical device and/or a medical device coating.

The present invention provides biodegradable polymers suitable for use as medical devices and coatings for medical devices. The polymers made in accordance with the teachings of the present invention are biodegradable, biocompatible, amphiphilic and derived from N-substituted 4-aza-caprolactone having the general formula directed below as Formula I:

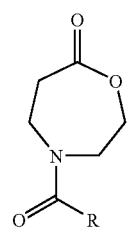

Formula 1 wherein R is a hydrogen, a straight chain or branched $C_1$-$C_{18}$ alkyl, a $C_3$-$C_{18}$ cycloalkyl, a straight chain or branched $C_2$-$C_{18}$ alkenyl or alkynyl, a straight chain or branched $C_1$-$C_{18}$ alkoxy, an aryl, protected carboxyl, a substituted or unsubstituted amino group, an amino acid residue, or hydroxyl. In one particular embodiment R is a methyl group.

The functional pendent group attached to the ring nitrogen provides the resulting polymer (following ring opening polymerization [ROP]) its amphiphilic properties. Moreover, even if left un-substituted, the ring nitrogen also provides the polymer backbone with a secondary amine which is a nucleophile center suitable for post-polymerization polymer modification. Thus the polymers of the present invention are extremely versatile.

In one embodiment of the present invention, N-substituted 4-aza-caprolactone (or its derivative) is copolymerized with D,L-lactide and L-lactide in the presence of an initiator with hydroxyl group(s) such as, but not limited to, poly(ethylene glycol) (PEG), 1,6-hexanediol and 1,8-octanediol and then subjected to a ring opening polymerization (ROP) using a suitable catalyst such as, but not limited to, Tin(II) 2-ethylhexanoate to form a polymer having the general structure according to Formula II:

gen, a straight chain or branched $C_1$-$C_{18}$ alkyl, a $C_3$-$C_{18}$ cycloalkyl, a straight chain or branched $C_2$-$C_{18}$ alkenyl or alkynyl, a straight chain or branched $C_1$-$C_{18}$ alkoxy, an aryl, protected carboxyl, a substituted or unsubstituted amino group, an amino acid residue, or hydroxyl. In one particular embodiment R is a methyl group.

In another embodiment of the present invention, N-substituted 4-aza-caprolactone (or its derivative) is copolymerized with D,L-lactide and L-lactide in the presence of an initiator with hydroxyl group(s) such as, but not limited to, polyethylene glycol) (PEG), 1,6-hexanediol and 1,8-octanediol and then subjected to ROP using a suitable catalyst such as, but not limited to, Tin(II) 2-ethylhexanoate to form a polymer having the general structure according to Formula III:

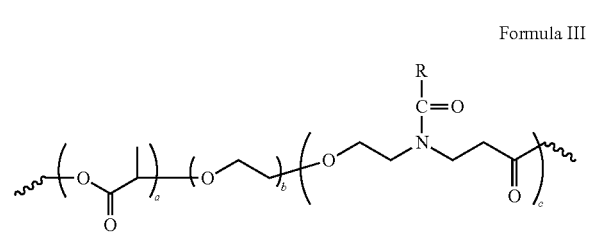

Formula III wherein a:b:c are repeating units and wherein a=0-20,000, b=1-2000 and c=1-20,000 and R is a hydrogen, a straight chain or branched $C_1$-$C_{18}$ alkyl, a $C_3$-$C_{18}$ cycloalkyl, a straight chain or branched $C_2$-$C_{18}$ alkenyl or a straight chain or branched $C_1$-$C_{18}$ alkoxy, an aryl, protected carboxyl, a substituted or unsubstituted amino group, an amino acid residue, or hydroxyl. In one particular embodiment R is a methyl group.

In another embodiment of the present invention, N-substituted 4-aza-caprolactone is subjected to ROP using a suitable catalyst such as, but not limited to, Tin(II) 2-ethylhexanoate to form a polymer having the monomer repeating unit for Formula V:

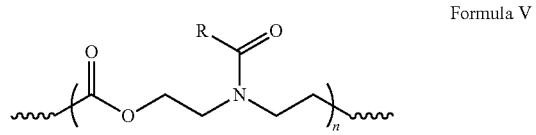

Formula V wherein R is a hydrogen, a straight chain or branched $C_1$-$C_{18}$ alkyl, a $C_3$-$C_{18}$ cycloalkyl, a straight chain or branched $C_2$-$C_{18}$ alkenyl or alkynyl, a straight chain or branched $C_1$-$C_{18}$ alkoxy, an aryl, protected carboxyl, a substituted or unsubstituted amino group, an amino acid residue, or hydroxyl; "n" is any integer from 1 to $10^4$. Moreover, it is also envisioned by the present inventors that N-substituted 4-aza-caprolactone can be co-polymerized with other compounds as disclosed supra such as, but not limited to, lactide,

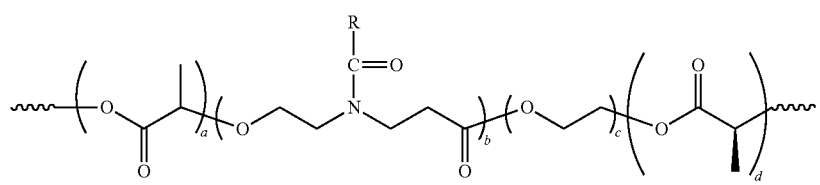

Formula II wherein a:b:c:d are repeating units and wherein a=0-20,000, b=1-20,000, c=1-2000 and d=0-20,000 and R is a hydroglycolide, δ-caprolactone, dioxanone, trimethyl carbonate, amino acids, peptides, and other to make amphiphilic biodegradable polymers in accordance with the teachings of the present invention. In one particular embodiment of the present invention the R is a hydrogen and the implantable medical device polymer comprises monomeric subunits made as follows:

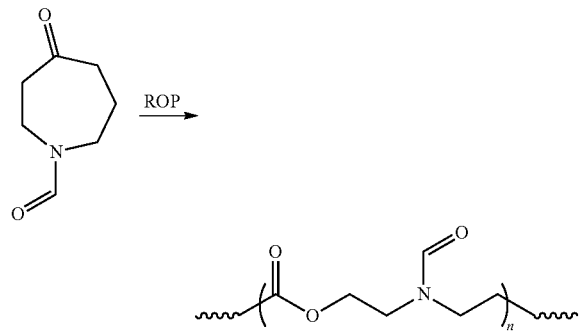

wherein "n" is an integer from 1 to $10^4$ and Formula Va comprises a hydrophilic polymer.

Thus the present invention provides at least two means for enhancing a medical device's biocompatibility and/or providing for in situ drug delivery to a treatment site. In one embodiment of the present invention the biocompatible, biodegradable, amphiphilic N-substituted 4-aza-caprolactone-based polymers made in accordance with the teachings of the present invention are used to provide coatings for implantable medical devices; the coating may or may not include a bioactive agent. In another embodiment of the present invention the entire medical device is made using the biocompatible, biodegradable, amphiphilic N-substituted 4-aza-caprolactone-based polymers made in accordance with the teachings of the present invention.

Biodegradable medical devices made in accordance with the teachings of the present invention include, but are not limited to, vascular stents, stent grafts, urethral stent, biliary stents, catheters, sutures, ocular devices, heart valves, shunts, pacemakers, bone screws and anchors, protective plates and prosthetic devices, both functional and cosmetic. The implantable medical device may be composed of the biodegradable, biocompatible polymers of the present invention, or may be coated with the polymers of the present invention. Moreover, in one embodiment of the present invention, the implantable medical device is made entirely from the biocompatible, biodegradable polymers of the present invention and is additionally coated with at least one polymer made in accordance with the teachings of the present invention.

Although myriad medical conditions can be treated and prevented using medical devices that are composed of, or incorporate, the coatings of the present invention, the present inventors have selected vascular stents and stent grafts as non-limiting enabling examples of the present invention. Thus, stents, stent coatings and method for using stents, coated and non-coated, will now be discussed in detail.

Vascular stents present a particularly unique challenge for the medical device coating scientist. Vascular stents (hereinafter referred to as "stents") must be flexible, expandable, biocompatible and physically stable. Stents are used to relieve the symptoms associated with coronary artery disease caused by occlusion in one or more coronary artery. Occluded coronary arteries result in diminished blood flow to heart muscles causing ischemia induced angina and in severe cases myocardial infarcts and death. Stents are generally deployed using catheters having the stent attached to an inflatable balloon at the catheter's distal end. The catheter is inserted into an artery and guided to the deployment site. In many cases the catheter is inserted into the femoral artery or of the leg or carotid artery and the stent is deployed deep within the coronary vasculature at an occlusion site.

Vulnerable plaque stabilization is another application for coated drug-eluting vascular stents. Vulnerable plaque is composed of a thin fibrous cap covering a liquid-like core composed of an atheromatous gruel. The exact composition of mature atherosclerotic plaques varies considerably and the factors that affect an atherosclerotic plaque's make-up are poorly understood. However, the fibrous cap associated with many atherosclerotic plaques is formed from a connective tissue matrix of smooth muscle cells, types I and III collagen and a single layer of endothelial cells. The atheromatous gruel is composed of blood-borne lipoproteins trapped in the sub-endothelial extracellular space and the breakdown of tissue macrophages filled with low density lipids (LDL) scavenged from the circulating blood. (G. Pasterkamp and E. Falk. 2000. Atherosclerotic Plaque Rupture: An Overview. J. Clin. Basic Cardiol. 3:81-86). The ratio of fibrous cap material to atheromatous gruel determines plaque stability and type. When atherosclerotic plaque is prone to rupture due to instability it is referred to as "vulnerable" plaque. Upon rupture the atheromatous gruel is released into the blood stream and induces a massive thrombogenic response leading to sudden coronary death. Recently, it has been postulated that vulnerable plaque can be stabilized by stenting the plaque. Moreover, vascular stents having a drug-releasing coating composed of matrix metalloproteinase inhibitor dispersed in, or coated with (or both) a polymer may further stabilize the plaque and eventually lead to complete healing.

Treatment of aneurysms is another application for drug-eluting stents. An aneurysm is a bulging or ballooning of a blood vessel usually caused by atherosclerosis. Aneurysms occur most often in the abdominal portion of the aorta. At least 15,000 Americans die each year from ruptured abdominal aneurysms. Back and abdominal pain, both symptoms of an abdominal aortic aneurysm, often do not appear until the aneurysm is about to rupture, a condition that is usually fatal. Stent grafting has recently emerged as an alternative to the standard invasive surgery. A vascular graft containing a stent (stent graft) is placed within the artery at the site of the aneurysm and acts as a barrier between the blood and the weakened wall of the artery, thereby decreasing the pressure on artery. The less invasive approach of stent-grafting aneurysms decreases the morbidity seen with conventional aneurysm repair. Additionally, patients whose multiple medical comorbidities place them at an excessively high risk for conventional aneurysm repair are candidates for stent-grafting. Stent-grafting has also emerged as a new treatment for a related condition, acute blunt aortic injury, where trauma causes damage to the artery.

Once positioned at the treatment site the stent or graft is deployed. Generally, stents are deployed using balloon catheters. The balloon expands the stent gently compressing it against the arterial lumen clearing the vascular occlusion or stabilizing the aneurysm. The catheter is then removed and the stent remains in place permanently. Most patients return to a normal life following a suitable recovery period and have no reoccurrence of coronary artery disease associated with the stented occlusion. However, in some cases the arterial wall's intima is damaged either by the disease process itself or as the result of stent deployment. This injury initiates a complex biological response culminating is vascular smooth muscle cell hyperproliferation and occlusion, or restenosis at the stent site.

Recently significant efforts have been devoted to preventing restenosis. Several techniques including brachytherapy, excimer laser, and pharmacological techniques have been developed. The least invasive and most promising treatment modality is the pharmacological approach. A preferred pharmacological approach involves the site-specific delivery of cytostatic or cytotoxic drugs directly to the stent deployment area. Site-specific delivery is preferred over systemic delivery for several reasons. First, many cytostatic and cytotoxic drugs are highly toxic and cannot be administered systemically at concentrations needed to prevent restenosis. Moreover, the systemic administration of drugs can have unintended side effects at body locations remote from the treatment site. Additionally, many drugs are either not sufficiently soluble, or too quickly cleared from the blood stream to effectively prevent restenosis. Therefore, administration of anti-restenotic compounds directly to the treatment area is preferred.

Several techniques and corresponding devices have been developed to deploy anti-restenotic compounds including weeping balloon catheters and injection catheters. Weeping balloon catheters are used to slowly apply an anti-restenotic composition under pressure through fine pores in an inflatable segment at or near the catheter's distal end. The inflatable segment can be the same used to deploy the stent or a separate segment. Injection catheters administer the anti-restenotic composition by either emitting a pressurized fluid jet, or by directly piercing the artery wall with one or more needle-like appendage(s). Recently, needle catheters have been developed to inject drugs into an artery's adventitia. However, administration of anti-restenotic compositions using weeping catheters and injection catheters to prevent restenosis remains experimental and largely unsuccessful. Direct anti-restenotic composition administration has several disadvantages. When anti-restenotic compositions are administered directly to the arterial lumen using a weeping catheter, the blood flow quickly flushes the anti-restenotic composition downstream and away from the treatment site. Anti-restenotic compositions injected into the lumen wall or adventitia may rapidly diffuse into the surrounding tissue. Consequently, the anti-restenotic composition may not be present at the treatment site in sufficient concentrations to prevent restenosis. As a result of these and other disadvantages associated with catheter-based local drug delivery, investigators continue to seek improved methods for the localized delivery of anti-restenotic compositions.

Figure 2:
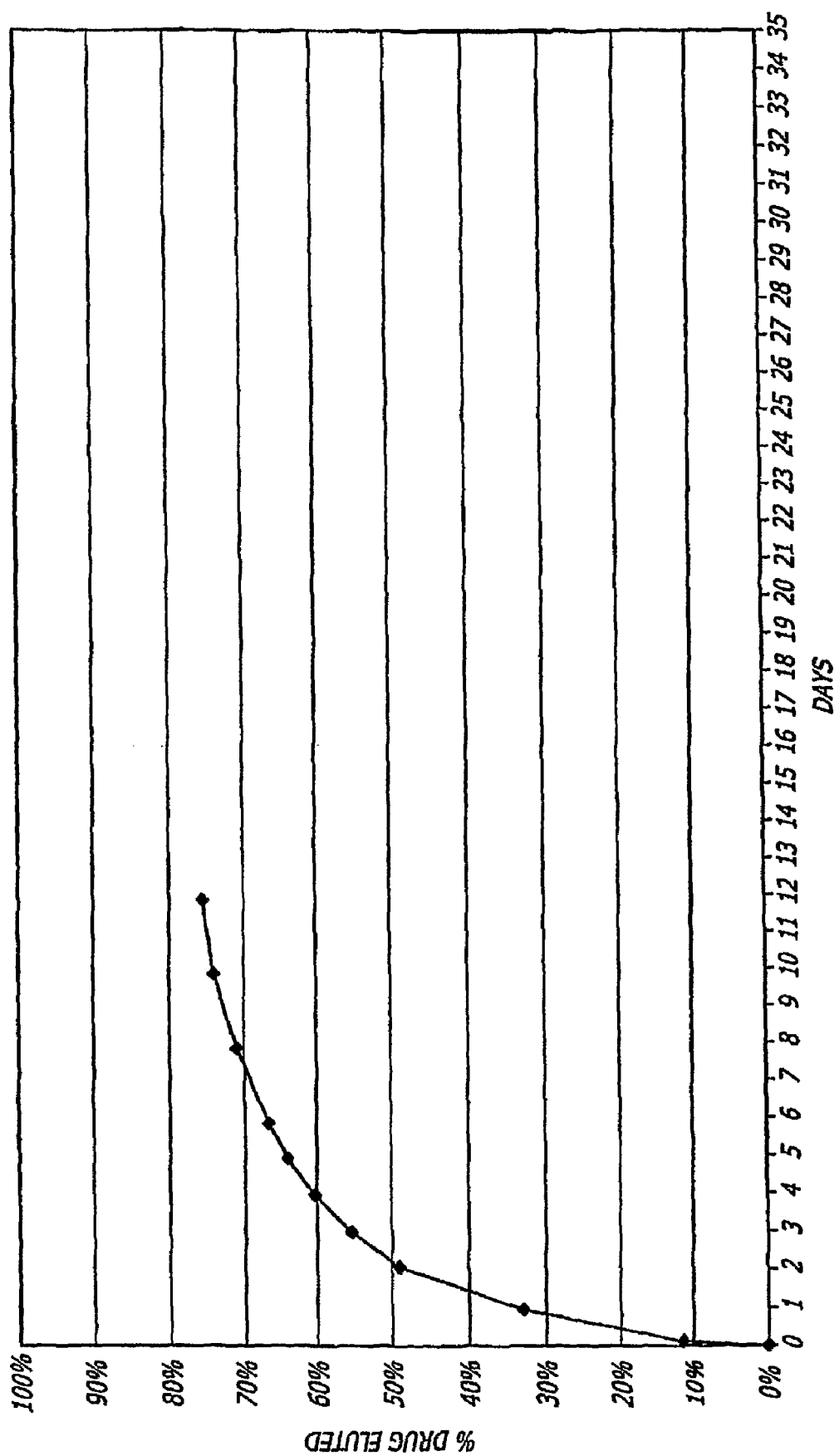
FIG. 2 graphically depicts idealized first-order kinetics associated with drug release from a polymer coating.
Figure 3:
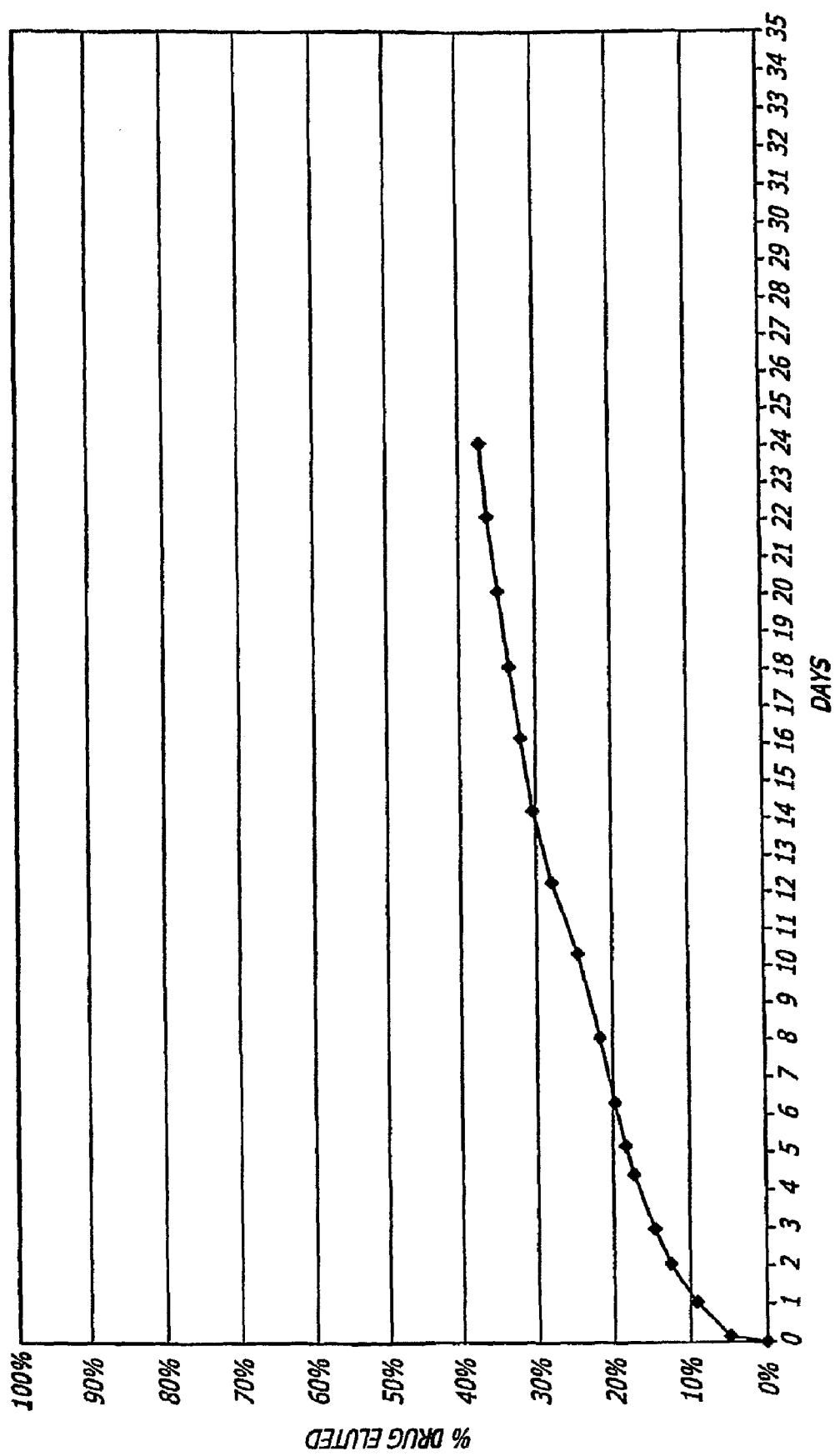
FIG. 3 graphically depicts idealized zero-order kinetics associated with drug release from a polymer coating.

The most successful method for localized anti-restenotic composition delivery developed to date is the drug-eluting stent. Many drug-eluting stent embodiments have been developed and tested. However, significant advances are still necessary in order to provide safe and highly effective drug delivery stents. One of the major challenges associated with stent-based anti-restenotic composition delivery is controlling the drug delivery rate. Generally speaking, drug delivery rates have two primary kinetic profiles. Drugs that reach the blood stream or tissue immediately after administration follow first-order kinetics. First-order drug release kinetics provide an immediate surge in blood or local tissue drug levels (peak levels) followed by a gradual decline (trough levels). In most cases, therapeutic levels are only maintained for a few hours. Drugs released slowly over a sustained time where blood or tissue concentrations remains steady follow zero-order kinetics. Depending on the method of drug delivery and tissue/blood clearance rates, zero-order kinetics result in sustained therapeutic levels for prolonged periods. Drug-release profiles can be modified to meet specific applications. Generally, most controlled release compositions are designed to provide near zero-order kinetics (see FIG. 3). However, there may be applications where an initial burst, or loading dose, of drug is desired (first-order kinetics, see FIG. 2) followed by a more gradual sustained drug release (near zero-order kinetics).

As discussed briefly supra, the biocompatible, biodegradable, amphiphilic polymers of the present invention are based on derivatives and co-polymers of N-substituted 4-aza-caprolactone having the general structure of Formula I. N-substituted 4-aza-caprolactone can be used alone to make the polymer of Formula V or it may be copolymerized with other known monomers to form biodegradable co-polymers of the present invention. Other known monomers include, but are not limited to, poly(lactide), poly(caprolactone), poly(glycolide), dioxanone, trimethylene carbonate, glycolide, amino acids, peptides and their derivatives. The following non-limiting Examples provide teachings for making representative biodegradable, biocompatible polymers of the present invention.

EXAMPLES

All of the reagents used in making the biodegradable, biocompatible polymers of the present invention are readily available from commercial sourced such as, but not limited to, Sigma-Aldrich Chemicals, St. Louis, Mo., USA. The common starting material, N-substituted 4-aza-caprolactone, can be purchased commercially or synthesized from 4-piperidone using methods know in the art.

Before proceeding further a note on nomenclature is in order. The term "N-substituted 4-aza-caprolactone" as used herein shall be used to generally describe the compound of Formula I. However, it is understood that it may also refer to compounds of Formulas VI wherein R=H and VII wherein R=CH$_3$ as follows:

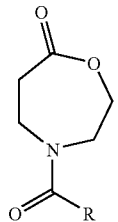

Formula I

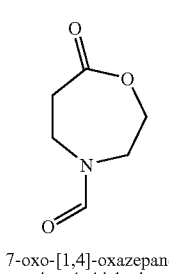

7-oxo-[1,4]-oxazepane-4-carbaldehyde

Formula VI

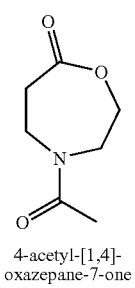

4-acetyl-[1,4]-oxazepane-7-one

Formula VII

Furthermore, it is understood that the compound of Formula I can be synthesized by Bayer-Villiger oxidation generally as follows using techniques known to those skilled in the art of synthetic organic chemistry:

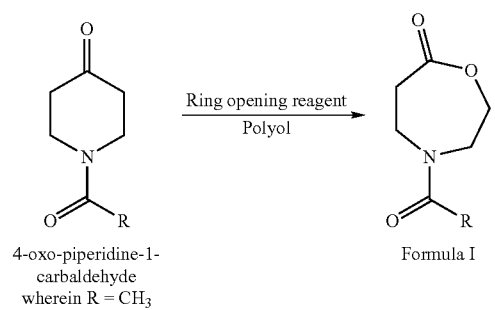

4-oxo-piperidine-1-carbaldehyde
wherein R = CH$_3$

Formula I

Example 1

Synthesis of Biodegradable Polymer of Formula III

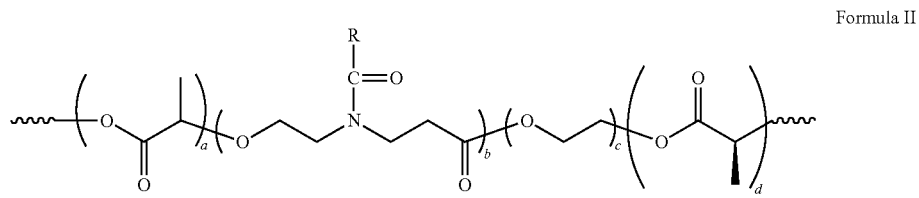

Formula II wherein a:b:c:d are repeating units and wherein a=0-20,000, b=1-20,000, c=1-2000 and d=0-20,000 and R is a hydrogen, a straight chain or branched $C_1$-$C_{18}$ alkyl, a $C_3$-$C_{18}$ cycloalkyl, a straight chain or branched $C_2$-$C_{18}$ alkenyl or alkynyl, a straight chain or branched $C_1$-$C_{18}$ alkoxy, an aryl, protected carboxyl, a substituted or unsubstituted amino group, an amino acid residue, or hydroxyl. In one particular embodiment R is a methyl group (D94).

In one embodiment of the present invention, the polymer of Formula II is referred to hereinafter as "D94" and is synthesized as follows: 0.5 gram of PEG-3400, 5 gram of D,L-lactide (3,6-dimethyl-1,4-dioxane-2,5-dione), 5 gram of L-lactide ((3s)-cis-3,6-dimethyl-1,4-dioxane-2,5-dione), 1 gram of 4-acetyl-[1,4]oxazepan-7-one (Formula I, R=methyl) and 0.12 gram of Tin (II) 2-ethyl hexanoate were added into a 100 mL glass serum bottle. A Teflon-coated magnetic stir bar was added into the bottle and the bottle was sealed with Teflon-coated silicon septum with crimpier. The reaction bottle was purged with nitrogen for 20 minutes and then placed in a 140° C. silicon oil bath with a stir bar in it for 72 hours. The reactant was dissolved in 20 mL chloroform and poured into about 200 mL of methanol for precipitation. This procedure was repeated three times. The final purified polymer was dissolved in chloroform and poured into a PTFE tray. The tray was placed in a vacuum oven at 50° C. overnight.

General Reaction for Making Polymer D94[1]

Example 2

Synthesis of biodegradable Polymer of Formula III

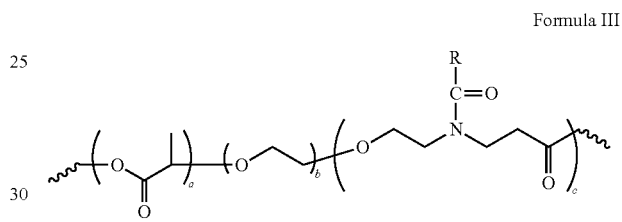

Formula III wherein a:b:c are repeating units and wherein a=0-20,000, b=1-2000 and c=1-20,000 and R is a hydrogen, a straight chain or branched $C_1$-$C_{18}$ alkyl, a $C_3$-$C_{18}$ cycloalkyl, a straight chain or branched $C_2$-$C_{18}$ alkenyl or a straight chain or branched $C_1$-$C_{18}$ alkoxy, an aryl, protected carboxyl, a substituted or unsubstituted amino group, an amino acid residue, or hydroxyl. In one particular embodiment R is a methyl group (D104).

In one embodiment of the present invention, the polymer of Formula III is referred to herein after as "D104" and is synthesized as follows: 0.5 gram of PEG-3400, 9 gram of D,L-lactide (3,6-dimethyl-1,4-dioxane-2,5-dione), 0.5 gram of

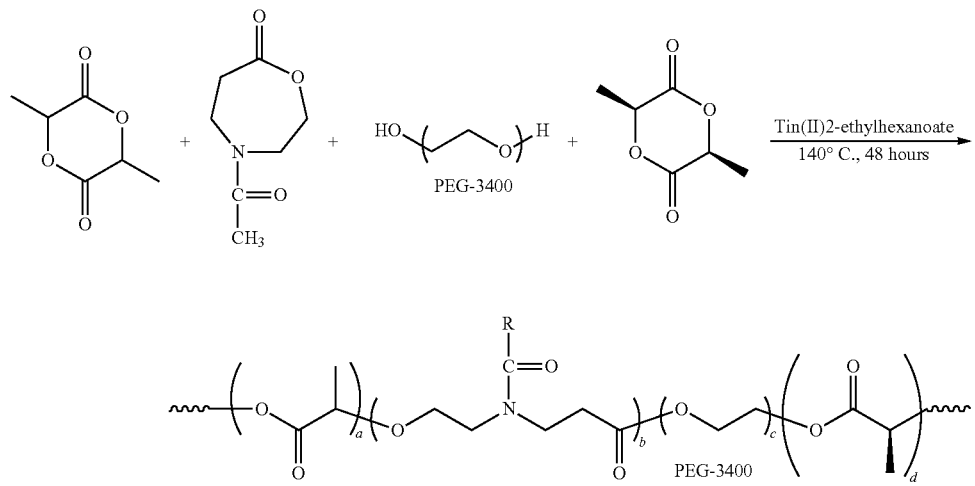

D94, a:b:c:d = 44:11.8:0.2:44

N-substituted 4-aza-caprolactone and 0.10 gram of Tin (II) 2-ethyl hexanoate were added into a 100 glass serum bottle. A Teflon-coated magnetic stir bar was added into the bottle and the bottle was sealed with a Teflon-coated silicon septum with crimpier. The reaction bottle was purged with nitrogen for 20 minutes and then placed in a 140° C. silicon oil bath with a stir bar in it for 72 hours. The reactant was dissolved in 20 mL chloroform and poured into about 200 mL of methanol for precipitation. This procedure was repeated three times. The final purified polymer was dissolved in chloroform and poured into a PTFE tray. The tray was placed in a vacuum oven at 50° C. overnight.

General Reaction for Making Polymer D104

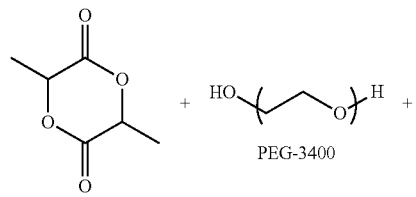

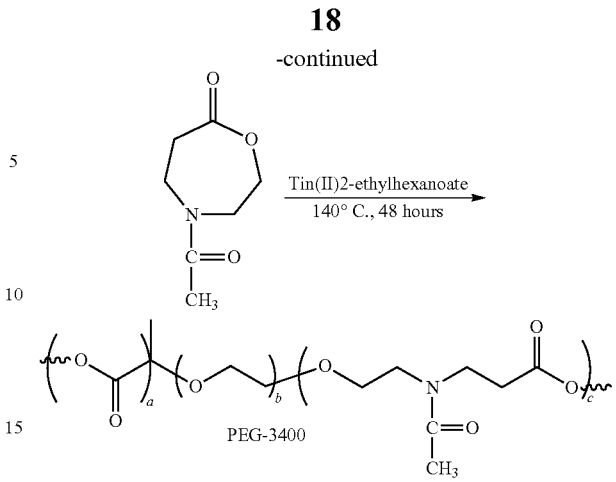

D104, a:b:c = 99:0.13:0.87

Example 3

Synthesis of Biodegradable Polymer Having the Formula IV

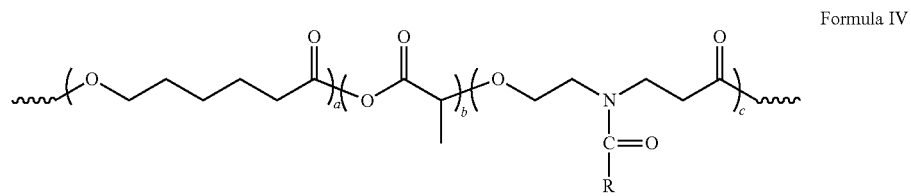

Formula IV wherein a:b:c are repeating units for each polymer and wherein a=0-20,000, b=1-20,000 and c=1-20,000 and R is a hydrogen, a straight chain or branched $C_1$-$C_{18}$ alkyl, a $C_3$-$C_{18}$ cycloalkyl, a straight chain or branched $C_2$-$C_{18}$ alkenyl or alkynyl, a straight chain or branched $C_1$-$C_{18}$ alkoxy, an aryl, protected carboxyl, a substituted or unsubstituted amino group, an amino acid residue, or hydroxyl. In one particular embodiment R is a methyl group (D105).

In one embodiment of the present invention, the polymer of Formula IV is referred to herein after as "D105" and is synthesized as follows: 9 gram of D,L-lactide (3,6-dimethyl-1,4-dioxane-2,5-dione), 0.5 gram of N-substituted 4-aza-caprolactone, 0.5 gram of ε-caprolactone and 0.10 gram of Tin (II) 2-ethyl hexanoate were add into a 100 mL glass serum bottle. A Teflon-coated magnetic stir bar was added into the bottle and the bottle was sealed with Teflon-coated silicon septum with crimpier. The reaction bottle was purged with nitrogen for 20 minutes and the placed in a 140° C. silicon oil bath with a stir bar in it for 72 hours. The reactant was dissolved in 20 mL chloroform and poured into about 200 mL of methanol for precipitation. This procedure was repeated three times. The final purified polymer was dissolved in chloroform and poured into a PTFE tray. The tray was placed in a vacuum oven at 50° C. overnight.

General Reaction for Making Polymer D105

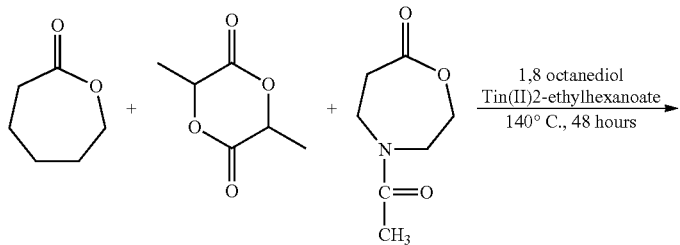

-continued

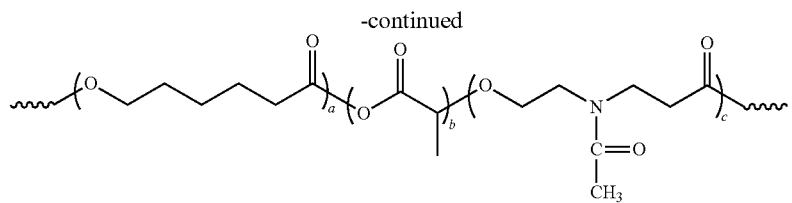

D105, a:b:c = 3:96:1

Example 4

Methods for Making Coatings for Implantable Medical Devices Using the Polymers of Examples 1-3: Co-Solvent of Drug/Polymer System (Drug Loading 30%)

Weigh 0.25 g of zotarolimus (formerly known as ABT-578) in a small-neck glass bottle. Add 25 mL of methylene chloride to the same bottle. Mix the solution until a clear solution is achieved. Weigh 0.25 g of degradable polymer made in accordance with the teachings of the present invention into a small weighing pan and transfer it into a same small neck bottle. Add 25 mL of methylene chloride into the bottle. Mix the solution as before until a clear solution is achieved. Using micropipette transfer 3 mL of zotarolimus/methylene chloride solution into a small-neck glass bottle. Using micropipette transfer 7 mL of polymer/methylene chloride solution into the same small-neck glass bottle. Mix the drug/polymer solution on a MAXMIXII mixer. Filter the drug/polymer solution through a 0.45 um PTFE filter into another pre-cleaned small-neck bottle.

The solution is then sprayed on a stent. Place the coated stent in a IIB2 hood overnight and weigh the dried post-coated stent.

Example 5

Methods for Making Coatings for Implantable Medical Devices Using the Polymers of Examples 1-3: Co-Solvent of Drug/Polymer System (Drug Loading 25%

Weigh 0.25 g of zotarolimus in a small-neck glass bottle. Add 25 mL of methylene chloride to the same bottle. Mix the solution until a clear solution is achieved. Weigh 0.25 g of degradable polymer made in accordance with the teachings of the present invention into a small weighing pan and transfer it into a same small-neck bottle. Add 25 mL of methylene chloride into the bottle. Mix the solution as before until a clear solution is achieved. Using a micropipette transfer 2.5 mL of zotarolimus/methylene chloride solution into a small-neck glass bottle. Using a micropipette transfer 7.5 mL of polymer/methylene chloride solution into the same small neck-glass bottle. Mix the drug/polymer solution on a MAXMIXII mixer. Filter the drug/polymer solution through a 0.45 um PTFE filter into another pre-cleaned small-neck bottle.

The solution is then sprayed on the stent. Place the coated stent in a IIB2 hood overnight and weigh the dried post-coated stent.

The present invention is directed at optimized drug releasing medical device coatings and medical devices themselves comprised entirely, or nearly entirely from biodegradable polymers of the present invention that are suitable for use in hemodynamic environments. The coatings and devices of the present invention may also have at least one bioactive compound or drug dispersed therein.

In addition to the aforementioned structural and drug-releasing profile considerations, polymers used as stent coatings must also be biocompatible. Biocompatibility encompasses numerous factors that have been briefly defined in the preceding "Definition of Terms" section. The need for a polymer to be biocompatible significantly limits the number of available options for the material scientist. Moreover, these options are further limited when the polymer coating is used on a device that is continuously exposed to hemodynamic forces. For example, stent coatings must remain non-thrombogenic, non-inflammatory and structurally stable for prolonged time periods.

Therefore, there are four specific attributes that the stent coating polymers made in accordance with the teachings of the present invention should possess. The polymer compositions of the present invention should be biocompatible, degrade at a predetermined rate, be elastic/ductile and possess a predetermined drug release profile. Other requirements include processing compatibility such as inert to sterilization methods including, but not limited to, ethylene oxide sterilization. The present invention provides novel polymer compositions made in accordance with the teachings of the present invention.

Release rate is not entirely a function of drug-polymer compatibility. Coating configurations, polymer swellability, and coating thickness also play roles. Moreover, the present invention provides yet another means for controlling drug elution rates. By tuning the biodegradable polymers of the present invention to degrade at a specific rate, drug elution can be precisely controlled and ceases entirely with the complete degradation of the polymer.

When the medical device of the present invention is used in the vasculature, the coating dimensions are generally measured in micrometers (μm). Coatings consistent with the teaching of the present invention may be a thin as 1 μm or a thick as 1000 μm. There are at least two distinct coating configurations within the scope of the present invention. In one embodiment of the present invention the drug-containing coating is applied directly to the device surface or onto a polymer primer. Depending on the solubility rate and profile desired, the drug is either entirely soluble within the polymer matrix, or evenly dispersed throughout. The drug concentration present in the polymer matrix ranges from 0.1% by weight to 80% by weight. In either event, it is most desirable to have as homogenous of a coating composition as possible. This particular configuration is commonly referred to as a drug-polymer matrix.

Finally, returning to coating thickness, while thickness is generally a minor factor in determining overall drug-release rates and profile, it is nevertheless an additional factor that can be used to tune the coatings. Basically, if all other physical and chemical factors remain unchanged, the rate at which a given drug diffuses through a given coating is directly proportional to the coating thickness. That is, increasing the coating thickness increases the elution rate and visa versa.

We now turn to another factor that contributes to the compatibilized, biodegradable controlled-release coatings of the present invention. As mentioned earlier, coating intended for medical devices deployed in a hemodynamic environment must possess excellent adhesive properties. That is, the coating must be stably linked to the medical device surface. Many different materials can be used to fabricate the implantable medical devices including, but not limited to, stainless steel, nitinol, aluminum, chromium, titanium, gold, cobalt, ceramics, and a wide range of synthetic polymeric and natural materials including, but not limited to, collagen, fibrin and plant fibers. All of these materials, and others, may be used with the controlled-release coatings made in accordance with the teachings of the present invention. Furthermore, the biodegradable polymers of the present invention can be used to fabricate an entire medical device such that the bioactive agent is dispersed throughout the polymer and released as the device degrades. This feature of the present invention is particularly useful when the device is implanted into remote regions of the body where subsequent removal, should it be required, is either not possible or involves complex, high risk surgical procedures.

Figure 4:
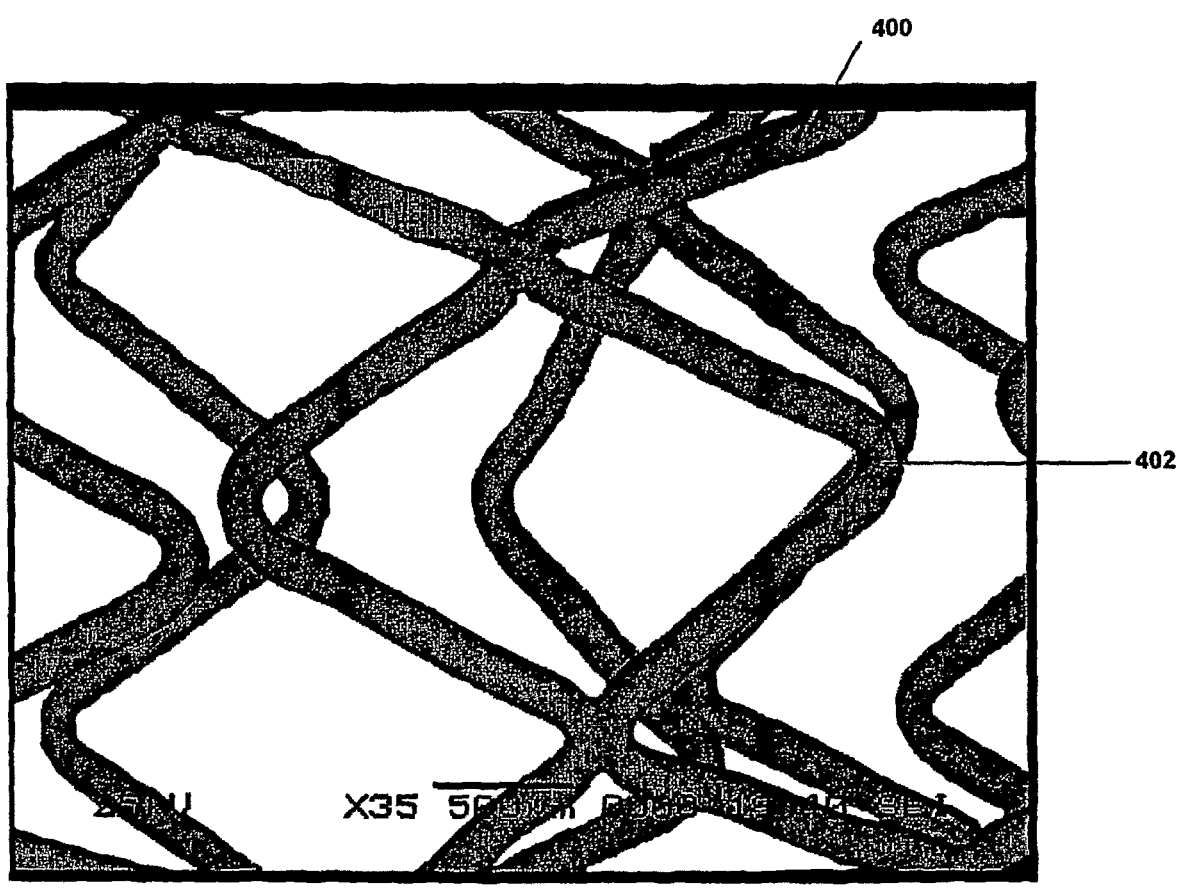
FIG. 4 depicts a vascular stent used to deliver the anti-restenotic compounds of the present invention.

One embodiment of the present invention is depicted in FIG. 4. In FIG. 4 a vascular stent 400 having the structure 402 is made from a material selected from the non-limiting group of materials including stainless steel, nitinol, aluminum, chromium, titanium, ceramics, and a wide range of synthetic polymeric and natural materials including collagen, fibrin and plant fibers. The structure 402 is provided with a coating composition made in accordance with the teachings of the present invention.

Figure 5:
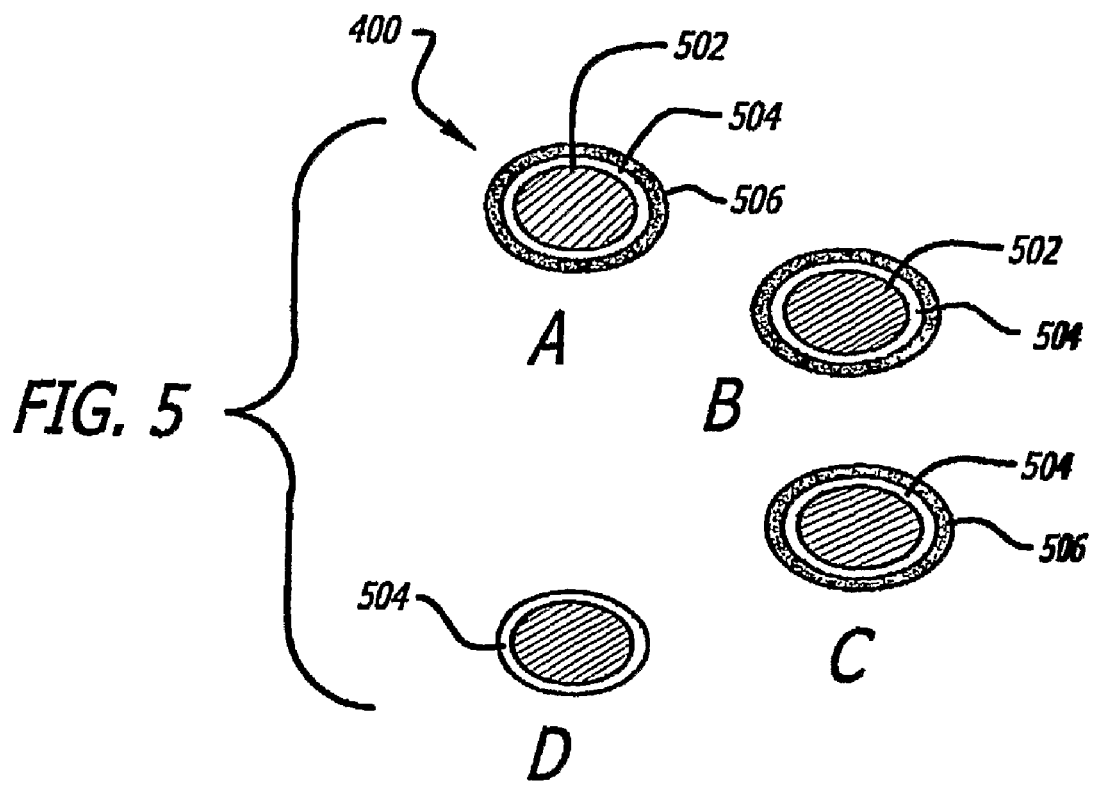
FIG. 5 depicts cross sections of medical devices (stents) having various drug-eluting coatings made in accordance with the teachings of the present invention.
Figure 6:
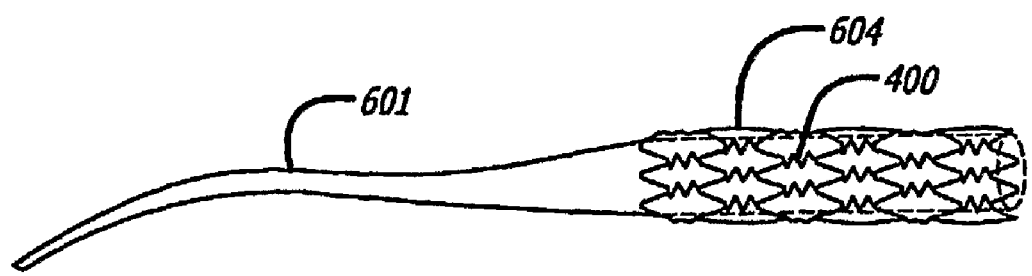
FIG. 6 depicts a balloon catheter assembly used for angioplasty and the site-specific delivery of stents to anatomical lumens at risk for restenosis.

FIG. 5a-d are cross-sections of stent 400 showing various coating configurations. In FIG. 5a stent 400 has a first polymer coating 502 comprising an optional medical grade primer, such as but not limited to parylene; a second controlled release coating 504; and a third barrier, or cap, coat 506. In FIG. 5b stent 400 has a first polymer coating 502 comprising an optional medical grade primer, such as but not limited to parylene and a second controlled release coating 504. In FIG. 5c stent 400 has a first controlled release coating 504 and a second barrier, or cap, coat 506. In FIG. 5d stent 400 has only a controlled release coating 504. FIG. 6 depicts a vascular stent 400 having a coating 604 made in accordance with the teachings of the present invention mounted on a balloon catheter 601.

There are many theories that attempt to explain, or contribute to our understanding of how polymers adhere to surfaces. The most important forces include electrostatic and hydrogen bonding. However, other factors including wettability, absorption and resiliency also determine how well a polymer will adhere to different surfaces. Therefore, polymer base coats, or primers are often used in order to create a more uniform coating surface.

The controlled-release coatings of the present invention can be applied to medical device surfaces, either primed or bare, in any manner known to those skilled in the art. Applications methods compatible with the present invention include, but are not limited to, spraying, dipping, brushing, vacuum-deposition, and others. Moreover, the controlled-release coatings of the present invention may be used with a cap coat. A cap coat as used here refers to the outermost coating layer applied over another coating. A drug-releasing copolymer coating is applied over the primer coat. A polymer cap coat is applied over the drug-releasing copolymer coating. The cap coat may optionally serve as a diffusion barrier to further control the drug release, or provide a separate drug. The cap coat may be merely a biocompatible polymer applied to the surface of the sent to protect the stent and have no effect on elution rates. One aspect of the present invention is a biodegradable cap coat that protects the device and bioactive agent from the environment until implanted is provided. After implantation is complete, the biodegradable cap coat degrades at a predetermined rate (made possible by the additional and modification of functional groups to the polymer backbone as made in accordance with the teachings of the present invention) exposing the medical device surface and bioactive agent to the physiological environment.

As discussed above, medical devices can be fabricated from the polymeric compounds of the present invention using a variety of methods. For exemplary, non-limiting, purposes a biodegradable vascular stent will be described. In the one embodiment the stent is a tubular shaped member having first and second ends and a walled surface disposed between the first and second ends. The walls are composed of extruded polymer monofilaments woven into a braid-like embodiment. In the second embodiment, the stent is injection molded or extruded. Fenestrations are molded, laser cut, die cut, or machined in the wall of the tube.

In the braided stent embodiment monofilaments are fabricated from polymer materials that have been pelletized then dried. The dried polymer pellets are then extruded forming a coarse monofilament which is quenched. The extruded, quenched, crude monofilament is then drawn into a final monofilament with an average diameter from approximately 0.01 mm to 0.6 mm, preferably between approximately 0.05 mm and 0.15 mm. Approximately 10 to approximately 50 of the final monofilaments are then woven in a plaited fashion with a braid angle about 90 to 170 degrees on a braid mandrel sized appropriately for the application. The plaited stent is then removed from the braid mandrel and disposed onto an annealing mandrel having an outer diameter of equal to or less than the braid mandrel diameter and annealed at a temperature between about the polymer glass transition temperature and the melting temperature of the polymer blend for a time period between about five minutes and about 18 hours in air, an inert atmosphere or under vacuum. The stent is then allowed to cool and is then cut.

The extruded tubular stent of the present invention is formed by first melting the pelletized polymer in the barrel of an injection molding machine and then injected into a mold under pressure where it is allowed to cool and solidify. The stent is then removed from the mold. The stent made in accordance with the teachings of the present invention may, or may not, be molded with fenestrations in the stent tube. In a preferred embodiment of the fenestrated stent, the tube blank is injection molded or extruded, preferably injection molded, without fenestrations. After cooling, fenestrations are cut into the tube using die-cutting, machining or laser cutting, preferably laser cutting. The resulting fenestrations, or windows, may assume any shape which does not adversely affect the compression and self-expansion characteristics of the final stent.

The stent is then disposed on an annealing mandrel having an outer diameter of equal to or less than the inner diameter of the stent and annealed at a temperature between about the polymer glass transition temperature and the melting temperature of the polymer blend for a time period between about five minutes and 18 hours in air, an inert atmosphere or under vacuum. The stent is allowed to cool and then cut as required.

Stents made in accordance with the teachings of the present invention have mechanical properties and strength that generally increase proportionally with the molecular weight of the polymers used. The optimum molecular weight range is selected to accommodate processing effects and yield a stent with desired mechanical properties and in vivo degradation rate.

Two physical qualities of the polymer or polymer blend used to fabricate the stent play important roles in defining the overall mechanical qualities of the stent: tensile strength and tensile modulus. Tensile strength is defined as the force per unit area at the breaking point. It is the amount of force, usually expressed in pounds per square inch (psi), that a substrate can withstand before it breaks, or fractures. The tensile modulus, expressed in psi, is the force required to achieve one unit of strain which is an expression of a substrate's stiffness, or resistance to stretching, and relates directly to a stent's self-expansion properties.

Tensile strength and tensile modulus are physical properties that define a self-expanding stent's performance characteristics; these properties include compression resistance and self-expansion, or radial expansion, force. Compression resistance relates to the stent's ability to withstand the surrounding tissue's circumferential pressure. A stent with poor compression resistance will not be capable of maintaining patency. Self expansion force determines the stent's capacity to restore patency to a constricted lumen once inserted. The combination of self-expansion with resistance to compression is competing qualities and must be carefully considered when a stent is designed Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A medical device comprising:
   a biodegradable polymer wherein at least one monomeric unit is derived from the compound of Formula I:

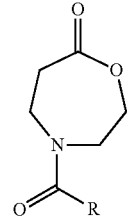

Formula I wherein R is a hydrogen, a straight chain or branched $C_1$-$C_{18}$ alkyl, a $C_3$-$C_{18}$ cycloalkyl, a straight chain or branched $C_2$-$C_{18}$ alkenyl or alkynyl, a straight chain or branched $C_1$-$C_{18}$ alkoxy, an aryl, protected carboxyl, a substituted or unsubstituted amino group, an amino acid residue, or hydroxyl.

2. The medical device according to claim 1 wherein R is a methyl group.

3. The medical device according to claim 1 wherein said medical device is selected from the group consisting of vascular stents, stent grafts, urethral stent, biliary stents, catheters, sutures, ocular devices, heart valves, shunts, pacemakers, bone screws and anchors, protective plates and prosthetic devices.

4. The medical device according to claim 1 wherein said biocompatible, biodegradable polymer further comprises a bioactive agent selected from the group consisting of zotarolimus, estrogens, chaperone inhibitors, protease inhibitors, protein-tyrosine kinase inhibitors, leptomycin B, peroxisome proliferator-activated receptor gamma ligands (PPARγ), hypothemycin, bisphosphonates, epidermal growth factor inhibitors, antibodies, proteasome inhibitors, antibiotics, anti-inflammatories, anti-sense nucleotides and transforming nucleic acids.

5. The medical device according to claim 1 wherein the biodegradable polymer comprises a compound according to Formula II:

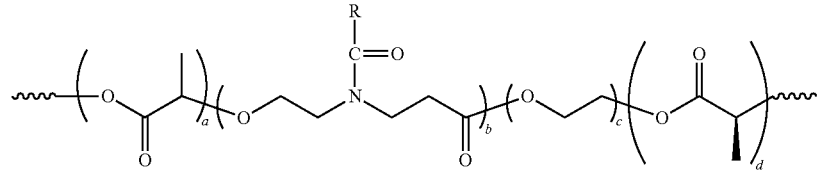

Formula II wherein a:b:c:d are repeating units and wherein a=0-20,000, b=1-20,000, c=1-2000 and d=0-20,000 and R is a hydrogen, a straight chain or branched $C_1$-$C_{18}$ alkyl, a $C_3$-$C_{18}$ cycloalkyl, a straight chain or branched $C_2$-$C_{18}$ alkenyl or alkynyl, a straight chain or branched $C_1$-$C_{18}$ alkoxy, an aryl, protected carboxyl, a substituted or unsubstituted amino group, an amino acid residue, or hydroxyl.

6. The medical device according to claim 5 wherein R is a methyl group and the repeating units are present in a ratio of 44:11.8:0.2:44; a:b:c:d respectively.

7. The medical device according to claim 1 wherein the biodegradable polymer comprises a compound according to Formula III:

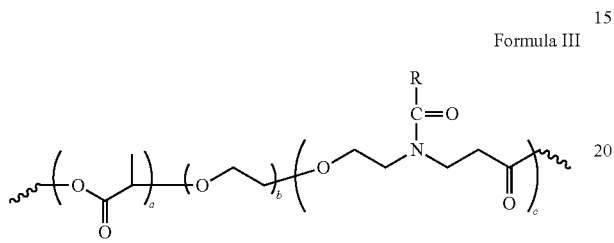

Formula III wherein a:b:c are repeating units and wherein a=0-20,000, b=1-2000 and c=1-20,000 and R is a hydrogen, a straight chain or branched $C_1$-$C_{18}$ alkyl, a $C_3$-$C_{18}$ cycloalkyl, a straight chain or branched $C_2$-$C_{18}$ alkenyl or alkynyl, a straight chain or branched $C_1$-$C_{18}$ alkoxy, an aryl, protected carboxyl, a substituted or unsubstituted amino group, an amino acid residue, or hydroxyl.

8. The medical device according to claim 7 wherein R is a methyl group and the repeating units are present in a ratio of 99:0, 13:0.87; a:b:c respectively.

9. The medical device according to claim 1 wherein the biodegradable polymer comprises a compound according to Formula IV:

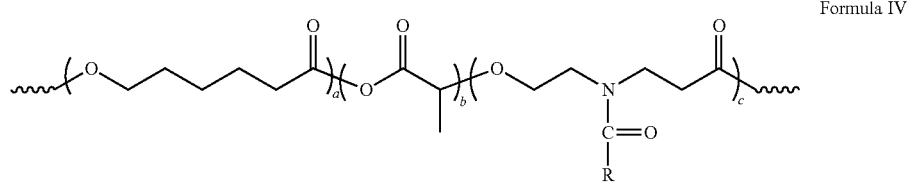

Formula IV wherein a:b:c are repeating units and wherein a=0-20,000, b=1-20,000 and c=1-20,000 and R is a hydrogen, a straight chain or branched $C_1$-$C_{18}$ alkyl, a $C_3$-$C_{18}$ cycloalkyl, a straight chain or branched $C_1$-$C_{18}$ alkenyl or alkynyl, a straight chain or branched $C_1$-$C_{18}$ alkoxy, an aryl, protected carboxyl, a substituted or unsubstituted amino group, an amino acid residue, or hydroxyl.

10. The medical device according to claim 9 wherein R is a methyl group and the repeating units are present in a ratio of 3:96:1; a:b:c respectively.

11. The medical device according to any one of claims 5 to 10 wherein said medical device is selected from the group consisting of vascular stents, stent grafts, urethral stem, binary stents, catheters, sutures, ocular devices, heart valves, shunts, pacemakers, hone screws and anchors, protective plates and prosthetic devices.

12. The medical device according to any one of claims 5 to 10 wherein said biocompatible, biodegradable polymer further comprises a bioactive agent selected from the group consisting of zotarolimus, estrogens, chaperone inhibitors, protease inhibitors, protein-tyrosine kinase inhibitors, leptomycin B, peroxisome proliferator-activated receptor gamma ligands (PPARγ), hypothemycin, bisphosphonates, epidermal growth factor inhibitors, antibodies, proteasome inhibitors, antibiotics, anti-inflammatories, anti-sense nucleotides and transforming nucleic acids.

13. A vascular stent comprising:
a biodegradable polymer wherein at least one monomeric unit is derived from the compound of Formula I:

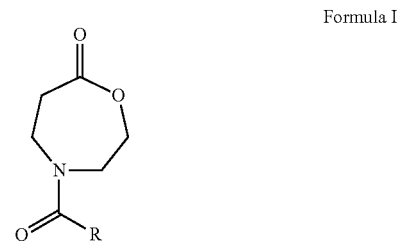

Formula I wherein R is a hydrogen and said biodegradable polymer further comprises a bioactive agent.

14. The vascular stent according to claim 13 wherein said bioactive agent is zotarolimus.

15. An implantable medical device having a controlled release coating comprising a biodegradable polymer wherein at least one monomeric unit is derived from the compound of Formula I:

Formula I wherein R is a hydrogen and said biodegradable polymer further comprises a zotarolimus.

16. The implantable medical device according to claim 15 wherein said medical device is a vascular stent made from a biocompatible material selected from the group consisting of stainless steel, nitinol, aluminum, chromium, titanium, gold, cobalt, cobalt alloys, titanium alloys, ceramics, and of synthetic polymers.

17. A biodegradable implantable medical device comprising a biodegradable polymer wherein at least one monomeric unit is derived from the compound of Formula I:

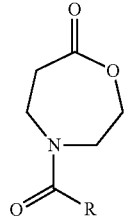

Formula I wherein R is a hydrogen and said biodegradable polymer further comprises a zotarolimus.

18. A vascular stent having a controlled-release coating comprising an amphiphilic, biocompatible, biodegradable polymer wherein at least one monomeric unit is derived from the compound of Formula I:

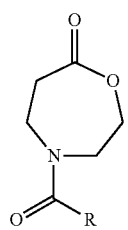

Formula I wherein R is a hydrogen and said biodegradable polymer further comprises a zotarolimus.

19. A biodegradable vascular stent comprising a biodegradable polymer wherein at least one monomeric unit is derived from the compound of Formula I:

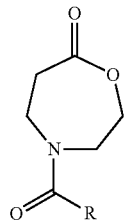

Formula I wherein R is a hydrogen and said biodegradable polymer further comprises a zotarolimus.

20. A monomer suitable for use in making a polymeric compound comprising the compound of Formula I:

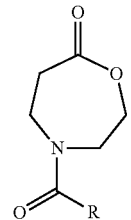

Formula I wherein R is a hydrogen, a straight chain or branched $C_1$-$C_{18}$ alkyl, a $C_3$-$C_{18}$ cycloalkyl, a straight chain or branched $C_2$-$C_{18}$ alkenyl or alkynyl, a straight chain or branched $C_1$-$C_{18}$ alkoxy, an aryl, protected carboxyl, a substituted or unsubstituted amino group, an amino acid residue, or hydroxyl.

21. A biodegradable polymer comprising a compound according to Formula II:

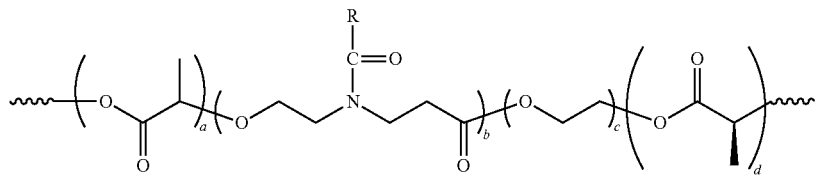

Formula II wherein a:b:c:d are repeating units and wherein a=0-20,000, b=1-20,000, c=1-2000 and d=0-20,000 and R is a hydrogen, a straight chain or branched $C_1$-$C_{18}$ alkyl, a $C_3$-$C_{18}$ cycloalkyl, a straight chain or branched $C_2$-$C_{18}$ alkenyl or alkynyl, a straight chain or branched $C_1$-$C_{18}$ alkoxy, an aryl, protected carboxyl, a substituted or unsubstituted amino group, an amino acid residue, or hydroxyl.

22. The biodegradable polymer according to claim 21 wherein R is a methyl group and the repeating units are present in a ratio of 44:11.8:0.2:44; a:b:c:d respectively.

23. A biodegradable polymer comprising a compound according to Formula III:

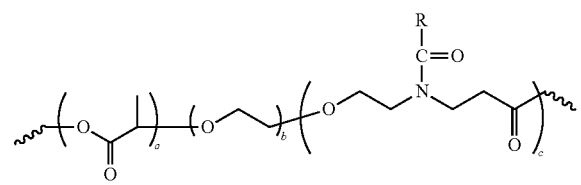

Formula III wherein a:b:c are repeating units and wherein a=0-20,000, b=1-2000 and c=1-20,000 and R is a hydrogen, a straight chain or branched $C_1$-$C_{18}$ alkyl, a $C_1$-$C_{18}$ cycloalkyl, a straight chain or branched $C_2$-$C_{18}$ alkenyl or alkynyl, a straight chain or branched $C_1$-$C_{18}$ alkoxy, an aryl, protected carboxyl, a substituted or unsubstituted amino group, an amino acid residue, or hydroxyl.

24. The biodegradable polymer according to claim 23 wherein R is a methyl group and the repeating units are present in a ratio of 99:0.13:0.87; a:b:c respectively.

25. A biodegradable polymer comprising a compound according to Formula IV:

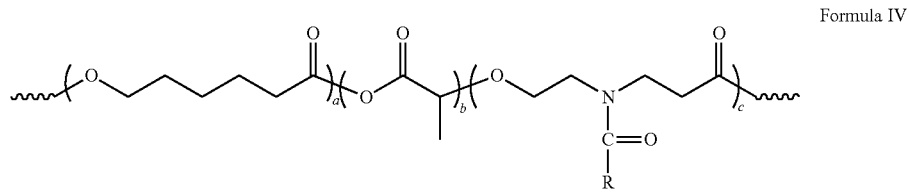

Formula IV wherein a:b:c are repeating units and wherein a=0-20,000, b=1-20,000 and c=1-20,000 and R is a hydrogen, a straight chain or branched $C_1$-$C_{18}$ alkyl, a $C_3$-$C_{18}$ cycloalkyl, a straight chain or branched $C_2$-$C_{18}$ alkenyl or alkynyl, a straight chain or branched $C_1$-$C_{18}$ alkoxy, an aryl, protected carboxyl, a substituted or unsubstituted amino group, an amino acid residue, or hydroxyl.

26. The biodegradable polymer according to claim 25 wherein R is a methyl group and the repeating units are present in a ratio of 396:1; a:b:c respectively.

27. A polymer comprising the monomer according to Formula I and at least one other polymer repeating unit selected from the group consisting of δ-caprolactone, dioxanone, trimethyl carbonate, amino acids, peptides and combinations thereof.

* * * * *

UNITED STATES PATENT AND TRADEMARK OFFICE
CERTIFICATE OF CORRECTION

PATENT NO. : 8,137,687 B2
APPLICATION NO. : 12/064108
DATED : March 20, 2012
INVENTOR(S) : Mingfei Chen, Peiwen Cheng and Kishore Udipi Page 1 of 1

It is certified that error appears in the above-identified patent and that said Letters Patent is hereby corrected as shown below:

IN THE CLAIMS:

Column 25, Claim 9, Line 52 Error Reads as "C1-C18 alkenyl";
should read as "C2-C18 alkenyl"

Column 25, Claim 11, Line 65 Error Reads as "hone screws";
should read as "bone screws"

Column 28, Claim 23, Line 60 Error Reads as "C1-C18 cycloalkyl";
should read as "C3-C18 cycloalkyl"

Column 29, Claim 26, Line 22 Error Reads as "396:1; a:b:c";
should read as "3:96:1; a:b:c"

Signed and Sealed this
Fourth Day of September, 2012

David J. Kappos
*Director of the United States Patent and Trademark Office*